United States Patent
Hananouchi et al.

(10) Patent No.: US 10,092,419 B2
(45) Date of Patent: Oct. 9, 2018

(54) SURGICAL INSTRUMENT FOR THE POSITIONING OF AN ALIGNMENT ELEMENT

(75) Inventors: Takehito Hananouchi, Hyogo (JP); Dieter Vangeneugden, Overpelt (BE)

(73) Assignee: MATERIALISE, NV, Leuven (BE)

( * ) Notice: Subject to any disclaimer, the term of this patent is extended or adjusted under 35 U.S.C. 154(b) by 932 days.

(21) Appl. No.: 13/180,688

(22) Filed: Jul. 12, 2011

(65) Prior Publication Data
US 2013/0018378 A1    Jan. 17, 2013

(51) Int. Cl.
| | |
|---|---|
| *A61B 17/17* | (2006.01) |
| *A61F 2/46* | (2006.01) |
| *A61B 90/11* | (2016.01) |
| *B33Y 80/00* | (2015.01) |
| *A61B 17/00* | (2006.01) |
| *A61B 17/56* | (2006.01) |
| *A61F 2/30* | (2006.01) |
| *A61B 34/10* | (2016.01) |

(52) U.S. Cl.
CPC ........ *A61F 2/4609* (2013.01); *A61B 17/1739* (2013.01); *A61B 17/1746* (2013.01); *A61B 90/11* (2016.02); *A61F 2/4612* (2013.01); *A61F 2/4657* (2013.01); *A61B 2017/00526* (2013.01); *A61B 2017/568* (2013.01); *A61B 2034/108* (2016.02); *A61F 2/30942* (2013.01); *A61F 2002/4677* (2013.01); *A61F 2002/4687* (2013.01); *B33Y 80/00* (2014.12); *Y10T 29/49* (2015.01)

(58) Field of Classification Search
CPC ............... A61B 17/17; A61B 17/1739; A61B 17/1703; A61B 17/1742; A61B 17/1746; A61B 17/175; A61B 17/1753; A61B 2017/1778; A61B 2017/320052
See application file for complete search history.

(56) References Cited

U.S. PATENT DOCUMENTS

| | | | | |
|---|---|---|---|---|
| 3,919,772 | A * | 11/1975 | Lenczycki | ............... 433/173 |
| 4,646,729 | A * | 3/1987 | Kenna et al. | ............... 606/88 |
| 4,719,907 | A * | 1/1988 | Banko et al. | ............... 606/96 |
| 5,976,149 | A | 10/1999 | Masini | |
| 6,273,891 | B1 | 8/2001 | Masini | |
| 6,416,553 | B1 * | 7/2002 | White et al. | ............... 623/22.38 |
| 7,981,158 | B2 * | 7/2011 | Fitz et al. | ............... 623/17.16 |
| 8,414,591 | B2 * | 4/2013 | De Smedt et al. | ............ 606/89 |

(Continued)

FOREIGN PATENT DOCUMENTS

| | | | |
|---|---|---|---|
| EP | 0353171 | A1 * | 1/1990 |
| EP | 1457159 | A1 * | 9/2004 |

(Continued)

OTHER PUBLICATIONS

The International Preliminary Report on Patentability, dated Jan. 23, 2014 in connection with PCT International Patent Application No. PCT/EP2012/063676.

(Continued)

*Primary Examiner* — Anu Ramana
(74) *Attorney, Agent, or Firm* — Patterson & Sheridan LLP

(57) ABSTRACT

The present invention relates to surgical instruments and methods for the manufacture thereof, for facilitating the positioning of an implant in a socket of a ball-and-socket joint, by positioning an alignment element such as a pin, wire, screw or drill.

12 Claims, 6 Drawing Sheets

(56) References Cited

U.S. PATENT DOCUMENTS

| | | |
|---|---|---|
| 8,608,749 B2 | 12/2013 | Meridew |
| 2004/0199258 A1 | 10/2004 | Macara |
| 2006/0161167 A1 | 7/2006 | Myers et al. |
| 2008/0262499 A1 | 10/2008 | Giori et al. |
| 2010/0016984 A1 | 1/2010 | Trabish |
| 2010/0023015 A1* | 1/2010 | Park ............................ 606/87 |
| 2010/0082035 A1 | 4/2010 | Keefer |
| 2010/0087829 A1 | 4/2010 | Metzger et al. |
| 2011/0093086 A1 | 4/2011 | Witt et al. |
| 2012/0179147 A1 | 7/2012 | Geebelen |
| 2012/0245647 A1 | 9/2012 | Kunz |
| 2013/0018378 A1 | 1/2013 | Hananouchi |

FOREIGN PATENT DOCUMENTS

| | | |
|---|---|---|
| WO | 2010124164 A1 | 10/2010 |
| WO | 2011029911 A1 | 3/2011 |
| WO | 2011060536 A1 | 5/2011 |

OTHER PUBLICATIONS

The International Search Report, dated Nov. 30, 2012 in connection with PCT International Patent Application No. PCT/EP2012/063676, 5 pages.

\* cited by examiner

SURGICAL INSTRUMENT FOR THE POSITIONING OF AN ALIGNMENT ELEMENT

FIELD OF THE INVENTION

The present invention relates to surgical instruments for positioning an alignment element based on pre-operational planning, as well as to methods for the manufacture thereof.

BACKGROUND

In most joint arthroplasty, replacement and/or reconstruction surgery procedures, and in particular in hip and shoulder joint surgery, a joint is replaced by a prosthetic implant. The main goal of such interventions is to relieve (arthritic) pain and/or to restore severe physical joint damage. When prosthesis fails, a revision surgery is carried out. However, this procedure is technically more difficult and time-consuming than the primary intervention and the outcome is often less satisfactory, both because there is less bone stock to work with and because the removal of adherent cement or prosthetic components may result in fracture or perforation of the bone. Furthermore, with each successive joint revision, the risk of infection and symptomatic loosening of the prosthesis may increase substantially. Accordingly, one of the most important aspects of joint surgery procedures is the correct, accurate and stable placement of the primary implant.

Correct implant placement is important in shoulder surgery, and particularly important in hip surgery. The majority of acetabular implants used in hip surgery are currently placed using the press-fit technique. In this technique, the patient's acetabulum is first reamed with a sequence of hemispherical reamers with increasing diameters, such that a hemispherical cavity is created at the location where the implant should be placed. The final (largest) reamer typically has a diameter smaller than that of the implant. In a further step, the implant is attached to an impactor and placed upon the pelvis of the patient, such that the implant supports on the rim of the reamed cavity and the orientation of the implant is anatomically suitable. Finally, the impactor is hit with a hammer until the implant sits inside the reamed cavity. Thereafter, the implant is released from the impactor.

The general consensus in the field is that the orientation of the implant determines the success of the surgery and the lifespan of the implant (Hayakawa et al., Archives of orthopedic and trauma surgery Vol. 129 (2009):1151-1156). However, the current procedure shows several shortcomings for obtaining a good orientation. Indeed, the only anatomical visual reference during final placement is the orientation of the transverse ligament (Pearse et al., Hip international Vol. 18 (2008):7-10), to which the top plane of the implant should be oriented in parallel. Accordingly, rotation around the axis of the transverse ligament remains a variable parameter. In addition, the transverse ligament is generally obscured from the surgeon's view, further hampering the orientation process. Furthermore, the impactor and hammer are both rather bulky, making it difficult to keep the impactor in a stable orientation.

Few practical solutions have been proposed for these problems. US patent application 2009/0163922 (Meridew, Metzger) describes a patient-specific guide to be positioned and optionally attached to the acetabular rim, designed to interface with the impactor so as to enforce the correct orientation. However, it is very doubtful whether such a device could be able to withstand the momentum applied to it during impaction.

Accordingly, there is a need for alternative and improved surgical devices, and in particular surgical guiding instruments, which provide the ability to correctly and accurately insert, place and orient an implant into a patient's joint.

SUMMARY OF THE INVENTION

The present invention relates to surgical instruments for use in arthroplasty. The instruments are intended for facilitating surgery on ball-and-socket joints in the human or animal body. In surgery on the human body, the instruments are therefore useful for hip and shoulder joint surgery, particularly for the positioning of an acetabular cup implant or glenoid implant. The surgical instruments allow for positioning of an alignment element, where the desired position of the alignment element is typically based on pre-operational planning. The alignment element can be an indicator pin, wire, screw or drill, which acts as a navigator for the surgeon to address an optimal pre-operationally planned implant alignment direction, in the reaming and/or the impacting phase of the surgical procedure.

The surgical instruments according to the present inventions are surgical fixtures. In a first aspect, the present invention provides surgical fixtures for positioning an alignment element. The fixtures according to the present invention comprise one or more patient-specific contact elements which fit onto areas on a socket of a ball-and-socket joint, onto areas around said socket and/or onto the rim of said socket in at least three contact points. Where the socket is a glenoid cavity, the areas around the socket may include the glenoidal rim and the periglenoidal region (e.g. infraglenoidal tuberculum, supraglenoidal tuberculum and collum scapulae, etc.) and might include the acromion and processus coracoideus (coracoid process). Where the socket is an acetabulum, the areas around the socket may include the periacetabular region (e.g. the limbus acetabuli, sulcus supra-acetabularis, superior ramus, etc.). The contact points have an arrangement wherein the angle between the line connecting one contact point and the center of the circle or ellipse best fitting the socket rim and the line connecting the adjacent contact point and said center is never greater than 180°. The surgical fixtures further comprise a positioning element which is attached to the fixture. This positioning element is provided with one or more holes which allow the insertion of the alignment element. Additionally, the positioning element is detachable from the rest of the fixture.

In particular embodiments, one (of the) contact element(s) is positioned on the fixture such that, when positioned on the bone, it interacts with an anatomical feature present on the rim of the socket or on the bone in or around the socket. In further embodiments, this anatomical feature is the posterior notch of the transverse ligament, or the coracoid process.

In certain embodiments, the surgical fixtures according to the present invention comprise at least two contact elements, or at least three contact elements. The contact elements then fit onto areas on the socket, around the socket and/or on the socket rim in at least three contact points, wherein the contact points have an arrangement wherein the angle between a line drawn between one contact point and the center of the circle or ellipse best fitting the socket rim and a line drawn between the adjacent contact point and said center is never greater than 180°. In further embodiments, the surgical fixture comprises at least two contact elements, wherein the positioning element corresponds to one of the contact elements.

As indicated hereabove, the positioning element is detachable from the rest of the fixture. In particular embodiments, the connection between the positioning element and the rest of the fixture is adapted or weakened, such that the positioning element can be detached fro the rest of the fixture by breaking said connection with surgical cutting elements. In other embodiments, the connection between the positioning element and the rest of the fixture is ensured by an element selected from a dovetail coupling, interlocking features, a pinned system and a snap-fit mechanism.

In particular embodiments, the surgical fixtures according to the present invention further comprise a connecting structure, wherein the positioning element and/or one or more of the one or more contact elements extend from the connecting structure.

As indicated hereabove, the positioning element comprises one or more holes. In certain embodiments, the position and/or direction of at least one hole is in accordance with pre-operational planning. In certain embodiments, at least one hole is part of a drill guide. In certain embodiments, the positioning element comprises a first and a second hole with a different diameter, wherein the first hole allows the insertion of the alignment element and wherein the second hole allows the insertion of a fixation element. In further embodiments, the positioning element comprises two or more holes which allow the insertion of a fixation element. In particular embodiments, the alignment element is selected from the group comprising a pin, a wire, a screw and a drill.

In particular embodiments, the surgical fixtures according to the present invention are manufactured via additive manufacturing.

In a further aspect, the present invention provides methods for the manufacture of the patient-specific surgical fixtures according to the present invention. The methods comprise the steps of:
  i. obtaining volume information of the socket of a ball-and-socket joint from a patient;
  ii. obtaining the installation direction of a socket implant for the patient;
  iii. identifying and selecting parts of the bone surrounding the implant zone which are suitable for inserting an alignment element;
  iv. identifying and selecting parts of the bone in or surrounding the implant zone which are suitable for use as a base for the contact surface or surfaces of the surgical fixture;
  v. designing and producing a surgical fixture based on the information obtained in steps i, ii, iii, iv and v.

In a further aspect, the present invention provides methods for guiding a socket implant in a socket of a ball-and-socket joint, comprising the steps of:
  1) positioning a surgical fixture according to the present invention onto the socket;
  2) using one of the holes provided by the fixture to insert a wire, pin, drill or screw into the bone surrounding the socket;
  3) removing the surgical fixture from the socket;
  4) using the wire, pin, drill or screw to guide the implant in the correct direction onto the socket according to the pre-operational planning.

In particular embodiments, step 1) involves a rotational movement of the fixture to obtain the desired orientation onto the socket and step 3) comprises detaching the positioning element from the rest of the fixture, and optionally from the bone, so as to allow thereafter, a reversal of the rotational movement of step 1) to remove the rest of the fixture from the bone.

The patient may be an animal or human patient. Therefore the socket may be any socket of a ball-and-socket joint in an animal or human body. In human patients, the socket of a ball-and-socket joint may be an acetabulum or a glenoid cavity. In particular embodiments, the socket is an acetabulum. In other embodiments, the socket is a glenoid cavity.

The surgical fixtures according to the present invention allow for a fast and accurate positioning of an indicator pin, wire, screw or drill, and allow for an efficient removal of the fixture from the anatomy after use.

BRIEF DESCRIPTION OF THE DRAWINGS

The following figures of specific embodiments of the invention are merely exemplary in nature and are not intended to limit the present teachings, their application or uses. Throughout the drawings, corresponding reference numerals indicate like or corresponding parts and features.

Figure 1:
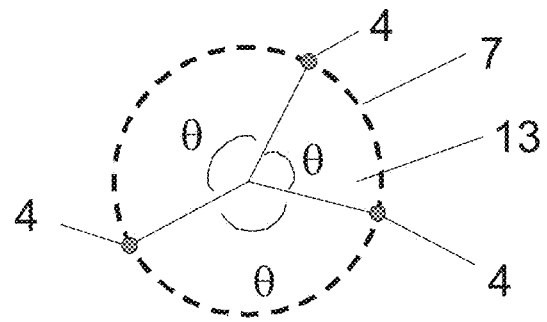
FIG. 1 A, A', A": Schematic representation of the relative position of patient-specific contact points (4) and their orientation relative to the acetabular rim (7) or glenoid cavity rim (16) and the acetabulum (13) or glenoid cavity (15) according to a particular embodiment of the present invention. B, B', B", C, C', C": Schematic representation of the arrangement and shape of patient-specific contact surfaces (14) and their orientation relative to the acetabular rim (7) or glenoid cavity rim (16) and the acetabulum (13) or glenoid cavity (15) according to a particular embodiment of the present invention.
Figure 1:
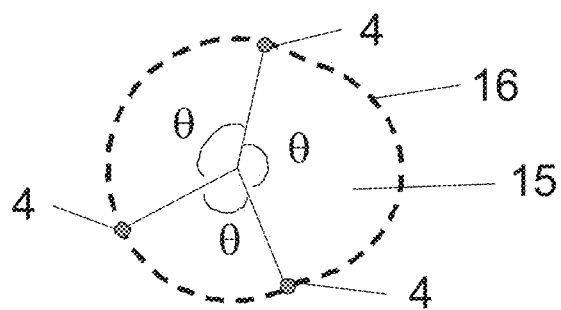
Figure 1:
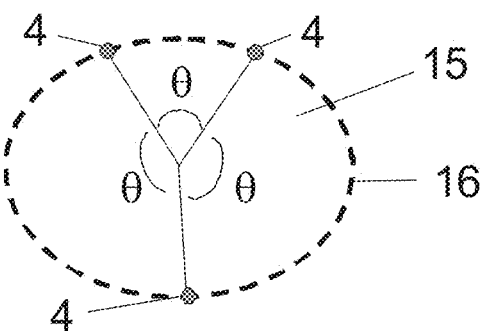
Figure 1:
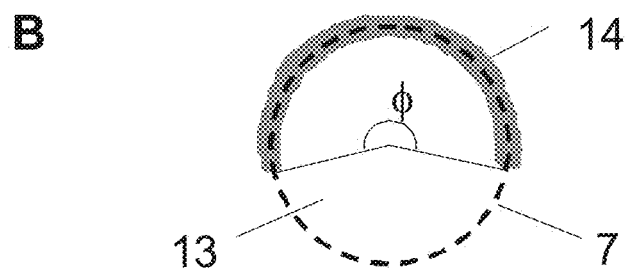
Figure 1:
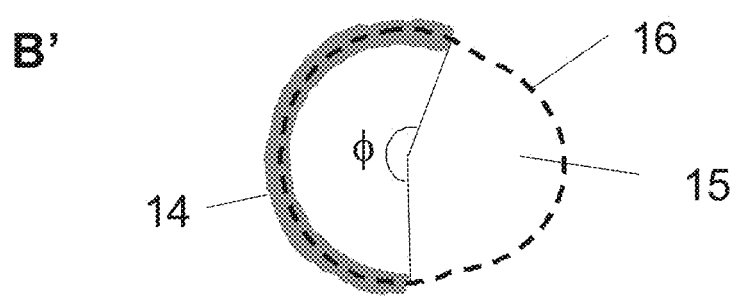
Figure 1:
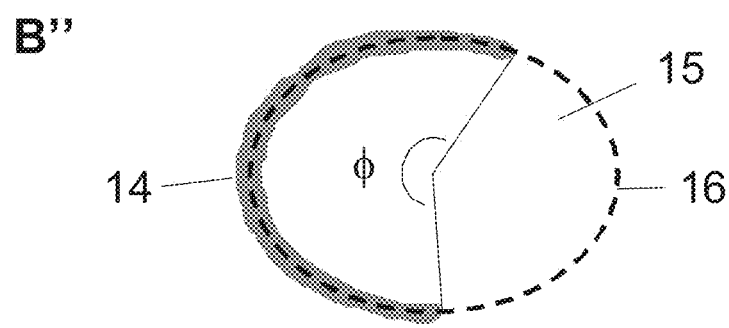
Figure 1:
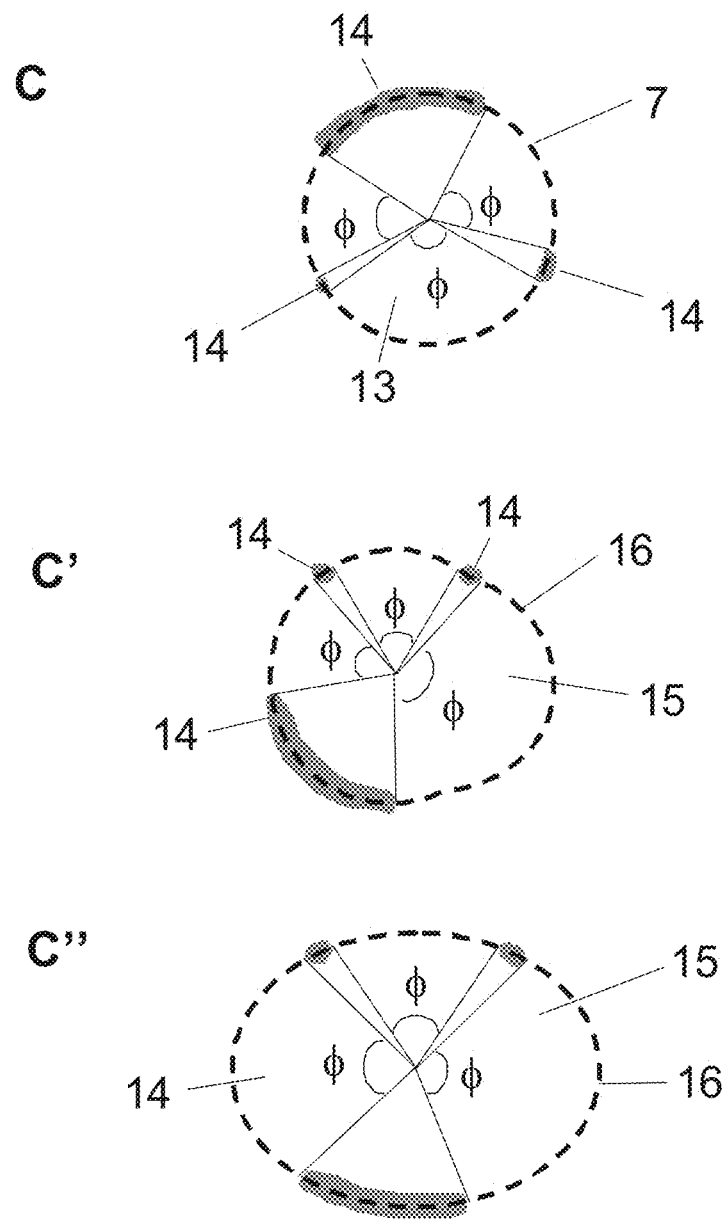

In the figures, the following numbering is used:
  1—surgical fixture; 2, 2'—contact element; 3—positioning element; 4—contact point; 5—hole for insertion of alignment element; 6—hole for fixation element; 7—acetabular rim; 8—posterior notch of the transverse ligament; 9—drill guide; 10—extension; 11—adapted connection; 12—connecting structure; 13—acetabulum; 14—contact surface; 15—glenoid cavity; 16—glenoid cavity rim; 17—pelvic bone

DETAILED DESCRIPTION

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

The present invention provides in a patient-specific surgical fixture for positioning an alignment element. The alignment element may be used for indicating a (pre-operationally planned) direction and/or position for an implant. The fixture comprises patient specific contact elements, which fit onto areas on or around a socket and/or socket rim; the fixture further comprises a positioning element for positioning the alignment element.

The present invention relates to the field of implant surgery, more particularly implants which are placed into a socket of a ball-and-socket joint. For human patients, this is an acetabular cup implant and/or a glenoid implant. The term "acetabular cup implant" as used herein refers to the component of a prosthetic hip implant which is placed into the acetabulum of a patient. The acetabulum is a concave surface of the pelvis, where the head of the femur meets with the pelvis, thus forming the hip joint. The term "glenoid implant" as used herein refers to a component of a prosthetic shoulder implant which is placed into or onto the glenoid cavity of a patient. Such implants may be used in a (total) shoulder arthroplasty or reverse (total) shoulder arthroplasty. The glenoid cavity, also known as glenoid fossa (of the scapula), is a shallow surface, which is located on the lateral angle of the scapula. This cavity forms the glenohumeral joint along with the humerus.

The terms "rim" and "socket rim" as used herein refer to the edge of a socket. Usually, this is a substantially convex edge of the concave bone surface which forms the socket. For human patients, particular examples are the acetabular rim and/or the glenoid rim. The term "acetabular rim" as used herein refers to the edge of the acetabulum, more particularly the substantially convex edge of the concave surface of the pelvis which forms the acetabulum. The term "glenoid rim" as used herein refers to the edge of the glenoid cavity, more particularly the substantially convex edge of the concave surface of the scapula which forms the glenoid cavity.

The term "socket" as used herein in the context of a ball joint, refers to a socket of a ball-and-socket joint of the human or animal body. For human patients, typical examples include the acetabulum and/or the glenoid cavity.

The term "alignment element" as used herein refers to an element which facilitates the correct positioning of an implant into or onto an anatomical socket, for example by indicating a certain location and/or direction for positioning and/or by physically guiding the implant or an implant guide to a certain location. Without such element, the implant may be positioned incorrectly, leading to suboptimal functioning of the prosthesis and discomfort to the patient.

The terms "surgical fixtures" and "fixture" as used herein refer to (patient-specific) surgical tools that can be positioned onto an anatomical part of a patient and that help a surgeon in the positioning of an alignment element.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect, the present invention provides surgical instruments for facilitating the positioning of an implant into or onto a socket of a ball-and-socket joint in the body of an animal or human patient. More particularly, in the context of humans, the present invention provides surgical fixtures for positioning an alignment element, which can be used for positioning an acetabular cup implant or a glenoid implant. The present invention is however equally useful for use in animals.

The surgical fixtures according to the present invention comprise at least one patient-specific contact element, i.e. a part of the surgical fixture which is used to ensure the correct positioning of the surgical fixture by contacting specific locations on the patient's anatomy.

The (one or more) patient-specific contact elements allow the surgeon to obtain the correct position of the surgical fixture onto the socket and/or socket rim, according to pre-operational planning. Indeed, the one or more contact element(s) fit onto specific areas on or around the socket and/or socket rim (with or without cartilage or other soft tissue) in at least three contact points. The contact points have an arrangement, preferably so as to surround the socket, whereby the angle between:

the line connecting one contact point and the center of the circle or ellipse best fitting the rim of the socket, and the line connecting the adjacent contact point and the center of the circle or ellipse best fitting the rim of the socket, is never greater than 180°.

In particular embodiments, the angle between the contact points (as determined by lines connecting each contact point with the center of the circle of ellipse) is never greater than 175, 170, 165, 160, 155, 150, 145, 140, 135, 130, 125, 120, 115, 110, 105, 100, 95 or 90°. This will be explained in further detail herein below.

The surgical fixtures according to the present invention further comprise a positioning element. The positioning element is a part of the fixture which is used for placing the alignment element onto or into the bone surrounding the socket in a pre-operationally planned position. The bone surrounding the socket suitable for placing the alignment element is, for example, the bone in the periacetabular region (e.g. the limbus acetabuli, sulcus supra-acetabularis, superior ramus, etc.) or periglenoidal region (e.g. infraglenoidal tuberculum, supraglenoidal tuberculum and collum scapulae, etc.). Therefore, the positioning element is provided with at least one hole or slit which either guides or allows the insertion of an alignment element. Together, the contact element(s) and the positioning element in the surgical fixture, allow for the correct positioning of an alignment element.

The fixtures of the present invention are characterized by the fact that the positioning element of the fixture is detachable, i.e. detachable from the rest of the surgical fixture. This can be ensured by the fact that the positioning element is attached to the surgical fixture by a connection which is weakened and/or adapted such that it can be easily broken, cut or removed using surgical instruments. Additionally or alternatively, the positioning element may be removably attached to the rest of the surgical fixture via features which allow a reversible connection of the positioning element, e.g. interlocking features, a dovetail coupling, a pinned system, a snap-fit system and the like. The fact that the positioning element is detachable facilitates the removal of the surgical fixture once the alignment element is positioned in the bone.

The desired position of the alignment element for guiding the placement of an implant is determined by pre-operative planning. Moreover, using preoperative planning optimal contact points for the contact element(s) of the surgical fixture according to the present invention can be determined. Indeed, while the number and shape of the contact elements may vary, the contact points comprised therein determine the stability of the fixture. The optimal position of the contact points ensures positional stability of the surgical fixture onto the socket. Specifically, to ensure positional stability of the fixture onto an acetabulum, the contact points have a circular or substantially circular arrangement, preferably so as to surround the acetabulum (13), wherein the angle θ defined by two adjacent contact points is never greater than 180°. In other words, the angle between the line connecting one contact point (4) and the center of the circle best fitting the acetabular rim (7) and the line connecting the adjacent contact point (4) and said center is never greater than 180°. This is shown in FIG. 1 A. Hereby the acetabulum is considered to have a substantially circular shape.

The glenoid cavity on the other hand, can be considered piriform. Thus, the glenoid cavity comprises a substantially circular shape on one side, but tapering towards the other side. Therefore, to ensure positional stability of the fixture onto a glenoid cavity (15), the contact points have a circular or substantially circular arrangement around the circumference of the rim of the glenoid cavity. More particularly, the angle θ formed by a first line drawn between one contact point (4) and the center of the circle best fitting the (substantially circular part of) the glenoid cavity rim (16) and a second line drawn between the adjacent contact point (4) and said center is never greater than 180°. This can also be expressed in terms of the sector angle defined by two adjacent contact points (4) which is never greater than 180°. This is shown in FIG. 1 A'.

Alternatively, the glenoid cavity may be considered as having a roughly elliptical shape. In that case, to ensure positional stability of the fixture onto a glenoid cavity (15), the contact points have an arrangement, wherein the angle θ between the (straight) line connecting one contact point (4) and the center of the ellipse best fitting the glenoid cavity rim (16) and the (straight) line connecting an adjacent contact point (4) and said center is never greater than 180°. Again this can be expressed by the fact that the sector angle defined by two adjacent contact points is never greater than 180° This is shown in FIG. 1 A".

Thus, more generally for an undefined socket, in the fixtures of the present invention, the contact elements fit onto the socket and/or socket rim by contacting said socket and/or rim at different contact points. The contact elements fit onto areas of (or around) a socket and/or a socket rim in at least three contact points, wherein the contact points have an arrangement, preferably so as to surround the socket, wherein the angle between a line drawn between one contact point and the center of the circle or ellipse best fitting the socket rim and a second line drawn between an adjacent contact point and said center is never greater than 180° or similarly the sector angle defined by two adjacent contact points is never greater than 180°. These contact points may all be located on the same contact element (i.e. one contact element comprises these three contact points), or distributed over two or more contact elements.

In certain embodiments, the one or more contact elements of the surgical fixtures according to the invention contain, on the surface which is intended for placement on the bone (with or without cartilage or other soft tissue), patient-specific surfaces, i.e. anatomy engagement surfaces which at least partially match the surface of (or around) the socket and/or the socket rim. This implies that the contact element comprises of a plurality of contact points (corresponding to a contact surface). The positional stability of the surgical fixture onto the acetabulum is then at least in part determined by the size and position of the contact surfaces on the contact element(s). The patient specific surface of a contact element typically spans an area which varies between one square micrometer ($\mu m^2$) and fifty square centimeters ($cm^2$).

In particular embodiments, the surgical fixtures according to the invention comprise only one contact element, which has a single contact surface. In this embodiment, the contact surface (14) spans the surface of the socket (13) and/or socket rim (7) over an angle φ of at least 180°, as schematically drawn for a circular socket (acetabulum) in FIG. 1 B. A piriform or elliptical socket (glenoid cavity) imposes a similar requirement (FIGS. 1 B' and B").

Alternatively, the surgical fixtures according to the invention may comprise more than one contact element comprising a patient-specific contact surface. A stable positioning of the surgical fixture can then be obtained if the contact surfaces of the different contact elements have an arrangement, on or around the socket (13) and/or socket rim (7), wherein for every pair of adjacent contact points not belonging to the same contact surface (14), the angle φ between the line drawn between one contact point and the center of the circle best fitting the socket rim (7) and a second line drawn between the adjacent contact point and said center is never greater than 180°, as schematically drawn for a circular socket (acetabulum) in FIG. 1 C. Again, a piriform or elliptical socket (glenoid cavity) imposes a similar requirement (FIG. 1 C' and C"). Also fixtures comprising combinations of one or more contact points with one or more contact surfaces are envisaged.

Alternative or specific combinations of the above are also envisaged. In certain embodiments, as indicated above, the surgical fixtures according to the present invention comprise only one contact element, which comprises several patient-specific contact points and/or contact surfaces. In other embodiments, the surgical fixtures according to the present invention comprise at least two contact elements, each comprising one or more patient-specific contact points and/or surfaces as described hereabove. In certain embodiments, the surgical fixtures according to the present invention comprise three contact elements, each comprising one or more patient-specific contact points and/or surfaces as described hereabove. In further embodiments, the surgical fixtures according to the present invention comprise four contact elements, each comprising one or more patient-specific contact points and/or surfaces as described hereabove. In yet further embodiments, the surgical fixtures according to the present invention comprise (at least) five, six, seven, eight, nine, ten or more contact elements, each comprising one or more patient-specific contact points and/or surfaces as described hereabove.

It will be understood to the skilled person that, in the fixtures as described herein the different contact elements of the surgical fixtures of the present invention need not make contact with the bone (with or without cartilage or other soft tissue) in the same way and need not contact the bone over their entire surface. Thus, in particular embodiments, at least one contact element contacts, at least partially, the socket rim via its contact point(s) and/or surface(s). In further embodiments, all contact elements contact, at least partially, the socket rim via the contact point(s) and/or surface(s) comprised therein. Specifically, in particular embodiments, the position and/or orientation of at least one contact element on the surgical fixture is patient-specific.

Figure 2:
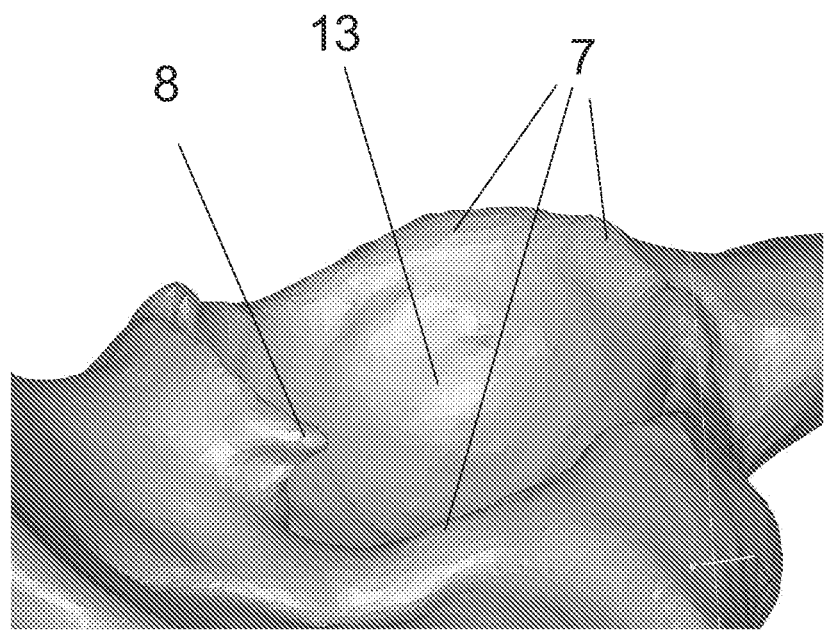
FIG. 2 Drawing of an acetabulum (13) surrounded by the acetabular rim (7) and the posterior notch of the transverse ligament (8).

Advantageously, at least one contact element is positioned on the fixture such that its patient-specific surface corresponds to the surface of the corresponding socket in the location of a conspicuous anatomical feature in or around the socket. For the acetabulum, this is for example the posterior notch of the transverse ligament, hereinafter also referred to as "posterior notch". The posterior notch of the transverse ligament (8) of the acetabulum (13) is drawn in FIG. 2. For the glenoid cavity, this is for example the coracoid process (processus coracoideus); this is a small hook-like structure on the lateral edge of the superior anterior portion of the scapula.

The provision of a contact element which fits into or against such a feature such as the posterior notch or the coracoid process ensures a stable fixation of the surgical fixture onto the socket. For instance, in particular embodiments, the fixture of the present invention is provided with a contact element fitting into the posterior notch. The device can be designed such that, in order to place the contact element within the notch, the surgical fixture according to the invention must be placed on the acetabulum in a first position whereby the contact element is placed next to the posterior notch. The desired final position of the surgical fixture onto the acetabulum is then obtained via a (slight) rotational movement, which allows the contact element to move into the notch until it reaches the rim of the notch. The contact between the contact element and the rim of the posterior notch of the transverse ligament ensures a rotational stop when the fixture is in the correct position. Thus, in particular embodiments, the surgical fixtures of the invention are designed such that they comprise at least one contact element which interacts with an anatomical feature in the socket, on the socket rim or on the bone (with or without cartilage or other soft tissue) surrounding the socket. Where the socket is a glenoid cavity, the bone surrounding the socket includes the glenoidal rim and the periglenoidal region (e.g. infraglenoidal tuberculum, supraglenoidal tuberculum and collum scapulae, etc.) and might include the acromion and coracoid process. Where the socket is an acetabulum, the bone surrounding the socket includes the periacetabular region (e.g. the limbus acetabuli, sulcus supra-acetabularis, superior ramus, etc.). In particular embodiments, the contact element is to be positioned within the posterior notch or the coracoid process. Specifically, one contact element is provided on the surgical fixture such that, when correctly positioned on the bone (i.e. in its final position), it fits within or onto the posterior notch or to the location of the coracoid process. More particularly, it is envisaged that, such a contact element grabs or locks onto the posterior notch or the coracoid process. This ensures a strong rotational stop when the fixture is in the correct position and therefore an accurate positioning of the fixture on the socket. Thus, in particular embodiments the shape of one contact element and its position on the fixture is such that, when positioned on the bone, it grabs onto or around the anatomical features such as the posterior notch or the coracoid process. Thus in particular embodiments such a contact element may be hook-shaped, such that it can grab on or around the anatomical feature. Thus, in particular embodiments one contact element is hook-shaped, or comprises a hook-shaped feature. In further particular embodiments, it is envisaged that the contact element which interacts with a specific anatomical feature on the rim of the socket or the surrounding bone may further also provide a locking feature. Indeed, the shape of this contact element may be adapted such that, when positioned on the bone, it snaps onto and thus in fact locks onto this feature.

The surgical fixtures of the present invention allow correct positioning of an alignment element by way of the positioning element. For this purpose, the positioning element of the fixtures of the invention comprises an opening or hole which allows the insertion of an alignment element which is guided by the positioning element into the bone surrounding the socket, such as the pelvic bone or scapula. The alignment element may be a wire, pin, screw or drill, particularly a metal wire, pin, screw or drill. In particular embodiments, the alignment element is a wire or a pin, particularly a Kirschner wire (K-wire) or a Hoffmann pin. In order to allow the guiding of the positioning of an implant for a socket of a ball-joint, the alignment element is typically positioned on the bone surrounding the socket, for example in the periacetabular area of the acetabulum (e.g. the limbus acetabuli, sulcus supra-acetabularis, superior ramus, etc.) or periglenoidal area of the glenoid cavity (e.g. infraglenoidal tuberculum, supraglenoidal tuberculum and collum scapulae, etc.) of the patient, in a direction parallel to the installation direction of the implant. For instance, for the positioning of an acetabular cup implant, the alignment element is typically positioned on the pelvic bone in a direction parallel to the installation direction of the acetabular implant. The optimal orientation of the opening of the positioning element can be obtained by determining the orientation of the positioning element according to pre-operational planning. Thus, in preferred embodiments, the direction and/or the position of at least one hole of the surgical fixtures of the invention which allows the insertion of an alignment element is in accordance with pre-operational planning. This allows the use of standard alignment elements such as K-wires. The positioning and/or orientation of the hole can be obtained via a certain location and/or orientation of the positioning element relative to the rest of the surgical fixture, via a certain location and/or position of the hole in the positioning element, or via a combination of the two. Additionally or alternatively, the shape of the alignment element itself can be provided such that, when inserted into the positioning element, it ensures the correct orientation to guide the implant.

Although the correct positioning of the surgical fixtures of the invention on the bone allows the insertion of an alignment element into the bone surrounding the socket as soon as the correct positioning of the surgical fixture is obtained, the insertion of the alignment elements is significantly facilitated if the surgical fixtures are (temporarily) fixed to the bone and/or locked into the correct position. Thus, in particular embodiments, the surgical fixtures may comprise fixation features such as holes, which allow for fixation of the surgical fixtures onto the bone, for example using screws, wires or pins. Thus, in particular embodiments, the surgical fixtures of the invention comprise at least one hole in addition to the hole which is meant for insertion of the alignment element. In particular embodiments, the surgical fixtures of the present invention comprise at least two holes. In certain embodiments, the hole(s) used as fixation features and the hole(s) used for insertion of the alignment element are located on the positioning element. In certain embodiments, the hole(s) used as fixation features and the hole(s) used for insertion of the alignment element are cylindrical. As both types of (cylindrical) holes have a different function, they may have a different diameter. The different diameter of the holes also avoids the surgeon from inserting the alignment element into a fixation feature, especially when the fixation features have a smaller diameter than the hole(s) for inserting an alignment element.

In the fixtures according to the invention, the positioning element and one or more contact element(s) may be separate units which are detachable. In particular embodiments, the positioning element is located onto or integrated in a contact element. A positioning element and a contact element may form a single unit, thus the positioning element may also function as a contact element. Where a positioning element is located onto a contact element, the hole(s) in the positioning element continue(s) through the contact element. In this way, the contact element does not block the insertion of fixation elements and/or alignment elements into the bone. Thus, in further embodiments, also the contact element(s) onto which a positioning element is located, contain at least one hole.

In some cases, the positioning of a second, or even a third alignment element allows an even more precise positioning of a socket implant. Thus, in particular embodiments, the surgical fixtures according to the present invention comprise more than one positioning element, of which at least one is detachable. In further embodiments, all positioning elements are detachable.

Insertion of the alignment element and/or fixation elements into the bone may be facilitated by first drilling a hole in the bone. The alignment element and/or fixation element(s) are then inserted into the hole drilled in the bone. Thus, in particular embodiments, at least one of the openings or holes on the positioning element (and the contact element(s) is part of a drill guide, which is located on the positioning element(s) or the contact element(s). In particular embodiments, the surgical fixture of the invention may be provided with a drill guide which can be positioned onto the hole.

In a particular embodiment, the surgical fixture according to the present invention is a disk (one contact element) comprising, on the side and/or edges for placement on the bone (with or without cartilage or other soft tissue), one or more contact points and/or contact surface(s) which match (i.e. specifically mate with) areas of (or around) the socket and/or the socket rim as described hereabove; and, on the opposing side, a positioning element. Advantageously, a less bulky fixture is obtained by omitting certain sectors from the disk, thus creating a surgical fixture containing two or more extensions, wherein each extension forms a contact element with one or more contact points and/or contact surfaces. The fact that certain contact elements are extensions increases grip on the fixture and visibility during the positioning of the fixture on the bone. Thus, in certain embodiments, the surgical fixtures according to the present invention comprise a connecting structure, wherein one or more contact elements extend from the connecting structure. In further embodiments, two or more contact elements extend from the connecting structure. Also the positioning element(s) may extend from the connecting structure. In certain embodiments, the connecting structure is a central element, particularly a central axis. In particular embodiments, the contact element(s) and/or the positioning element(s) are separate units which are connectable to the connecting structure, central element or axis. In alternative embodiments, the surgical fixtures of the present invention are manufactured as a single piece.

Once the alignment element is inserted into the bone via the positioning element(s), the surgical fixture must be removed from the socket in order to proceed with the surgery, e.g. to insert the socket implant. However, the inserted alignment element (and/or fixation elements) may limit the mobility of the surgical fixture, particularly when in the final position of the fixture one of the contact elements contacts or grabs an anatomical feature such as the posterior notch or the coracoid process. To overcome this problem the present invention provides that in the surgical fixtures of the invention at least one positioning element on the surgical fixture is detachable. Additionally, one or more contact elements may be detachable.

In order to ensure a detachable positioning element or contact element, the present invention envisages embodiments wherein the connection between the positioning or contact element and the rest of the fixture is adapted or weakened to make the positioning or contact element detachable, while still maintaining the required rigidity to assure correct positioning. Thus, in particular embodiments, the connection between at least one positioning element or contact element and the rest of the fixture is adapted and/or weakened such that it can be detached from the guide with surgical cutting instruments. In certain embodiments, this connection is located on an extension of the connecting structure as described hereinabove.

Alternatively, the one or more positioning elements and/or contact elements may be removably connected to the rest of the fixture via a specific mechanism such as a dovetail coupling, interlocking features, a pinned system, a snap-fit system, or a combination thereof. This avoids the use of surgical cutting instruments. Moreover, if the connection between the positioning element(s) and/or the contact element(s) and the rest of the fixture is a standard connecting feature, the positioning element(s) can be reused on another surgical fixture. In certain embodiments, this connection is located on an extension of the connecting structure as described hereabove.

In particular embodiments, the surgical fixtures of the present invention further comprise one or more extensions on the fixture which do not contain a contact element or positioning element. Such extensions as such do not contribute to the fit of the fixture on the bone but may allow an enhanced grip of the surgeon on the surgical fixtures, and may for example facilitate the rotational movement of the surgical fixture during its positioning, or facilitate the removal of the fixture after the positioning of the alignment element. For further facilitation of the rotational movement, such extensions may comprise a screw drive, i.e. a feature that allows the extension (and thus fixture) to be turned with a screw driver, hex key, or the like. Alternatively, the screw drive is not positioned on an extension, but elsewhere on the fixture.

In a further aspect, the present invention provides methods for the manufacture of the surgical fixtures described herein.

The surgical fixtures according to the present invention comprise one or more patient-specific contact points and/or surfaces. Also the position and/or orientation of the positioning element(s) and/or the contact elements may be patient-specific. The generation of patient-specific surgical fixtures is done based on pre-operative images of the bone area (with or without cartilage or other soft tissue) surrounding the socket of the ball joint under consideration (e.g. the pelvic bone or the scapula), and planning of the surgery. More particularly, the generation of patient-specific surgical fixtures is done based on pre-operative images of the socket (e.g. the acetabulum or the glenoid cavity), and planning of the surgery. Accordingly, methods for producing the surgical fixtures according to the present invention typically comprise the steps of:

i. Obtaining volume information of a socket, e.g. the acetabulum or glenoid cavity, from a patient.
ii. Obtaining the installation direction of the socket implant for the patient.
iii. Identifying and selecting parts of the bone (with or without cartilage or other soft tissue) surrounding the implant zone which are suitable for inserting an alignment element.
iv. Identifying and selecting parts of the bone in or surrounding the implant zone which are suitable for use as a base for the contact points and/or contact surface(s) of the surgical fixture.
v. Designing and producing a surgical fixture based on the information obtained in steps i, ii and iii.

The step of obtaining volume information of the socket typically comprises obtaining digital patient-specific image information which can be done by any suitable means known in the art, such as for example a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002.

In a particular embodiment, Additive Manufacturing (AM) techniques are used for manufacturing the surgical fixtures according to the invention, or parts thereof. AM techniques are particularly useful to manufacture patient-specific contact surfaces, or to produce the surgical fixtures in one piece. As an example, the manufacturing of medical-image-based patient-specific surgical instruments via AM is described in U.S. Pat. No. 5,768,134 (Swaelens et al).

AM can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The surgical fixtures according to the present invention may be manufactured in different materials. Typically, only materials that are biocompatible (e.g. USP class VI compatible) with the animal or human body are taken into account. Preferably the surgical fixture is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

A further aspect of the present invention provides methods for using the surgical fixtures described herein. More particularly, the present invention provides methods for guiding an implant in a socket of a ball joint such as an acetabulum or glenoid cavity. The methods comprise the steps of:

1) Positioning a surgical fixture as described herein onto the socket, e.g. acetabulum or glenoid cavity. In certain embodiments, this step involves a (slight) rotational movement of the surgical fixture. The rotational movement facilitates obtaining the desired (pre-operationally planned) orientation of the fixture onto the socket;
2) Optionally fixing the surgical fixture onto the socket. This step is only possible if the surgical fixture comprises holes for inserting one or more fixation elements;

3) Using one of the holes provided by the positioning element of the surgical fixture to insert a pin, wire, drill or screw into the bone surrounding the socket;
4) Removing said surgical fixture from the socket, and
5) Using the pin, wire, drill or screw of step 3) to obtain the correct implant direction; this is the direction according to the pre-operational planning.

In particular embodiments, where step 1) involves a rotational movement of the fixture to obtain the desired orientation onto the socket, step 4 will comprise detaching said positioning element from the rest of the fixture and from the socket, so as to allow thereafter, a reversal of the rotational movement of step 1) to remove the rest of the fixture from the socket.

It is noted that the alignment element envisaged in the context of the present invention may be used as a visual alignment element or a physical alignment element. In particular embodiments, the alignment element is a pin or wire and is used as a physical alignment element to guide an implant or implant guide onto the bone in the correct position. Typically the implant or implant guide will comprise a hole or slit which is positioned such that, when the hole or slit of the implant or implant guide is mated with the alignment feature, it will guide the implant and/or implant guide directly in the desired position on the socket of the ball joint.

The invention will now be illustrated by the following, non-limiting illustrations of particular embodiments of the invention.

EXAMPLES

Example 1

Surgical Fixture with Multiple Contact Elements

Figure 3:
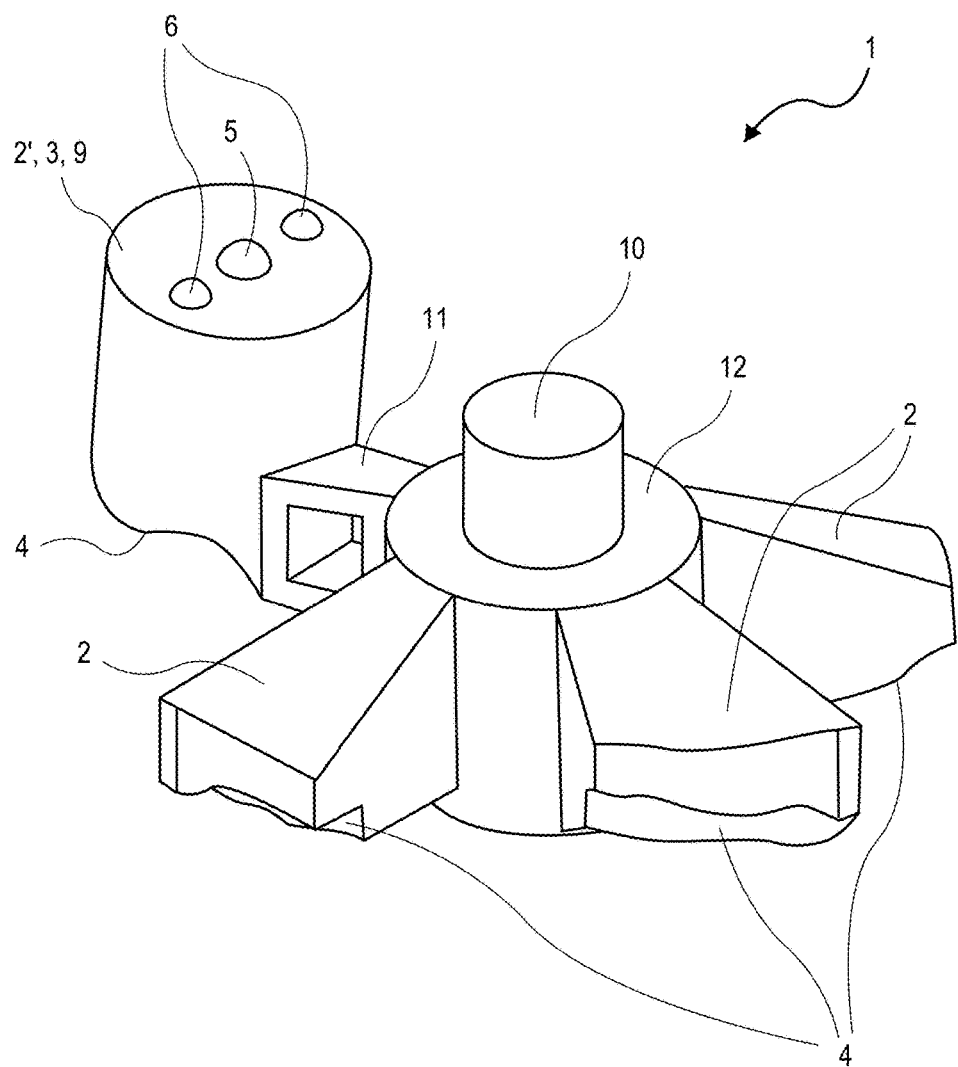
FIG. 3 Surgical fixture (1) according to a particular embodiment of the present invention, comprising a connecting structure (12), a positioning element (3) and four contact elements (2, 2'), each comprising a contact surface (4). The fixture further comprises an extension (10). The positioning element (3) is also a drill guide (9), comprises holes (5, 6) and is connected to the rest of the fixture via a weakened connection (11).

The surgical fixtures according to the present invention may comprise more than one contact element. FIG. 3 shows such a surgical fixture (1) according to a particular embodiment of the present invention. The fixture comprises a positioning element (3) and four contact elements (2, 2'), each comprising a patient-specific contact surface (4). The positioning element forms a single unit with one of the contact elements (2'), and comprises a hole (5) for insertion of an alignment element and holes (6) for insertion of fixation elements. The hole (5) for insertion of an alignment element may also be used for drilling a hole in the pelvic bone. Thus, the positioning element is also a drill guide (9), more particularly a drilling cylinder. Each of the contact elements (2, 2') extends from a connecting structure (12). The connection (11) between the positioning element (3) and the connecting structure (12) is adapted, such that the positioning element can be easily detached from the surgical fixture with surgical cutting instruments. The surgical fixture (1) further comprises an additional extension (10), which allows for an enhanced grip on the fixture.

Example 2

Surgical Fixture with One Contact Element

Figure 4:
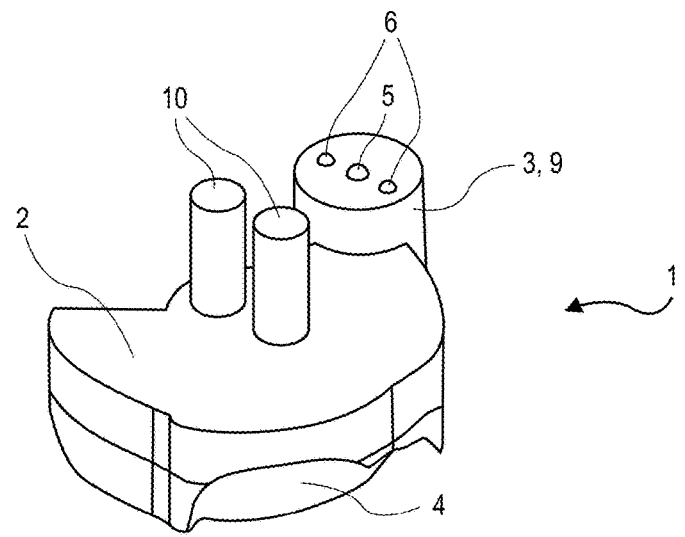
FIG. 4 A: Surgical fixture (1) according to a particular embodiment of the present invention, comprising a positioning element (3) and a contact element (2) comprising a contact surface (4). The fixture further comprises two extensions (10). The positioning element (3) is also a drill guide (9), comprises holes (5, 6). B: the same surgical fixture (1) positioned on an acetabulum of a pelvic bone (17).
Figure 4:
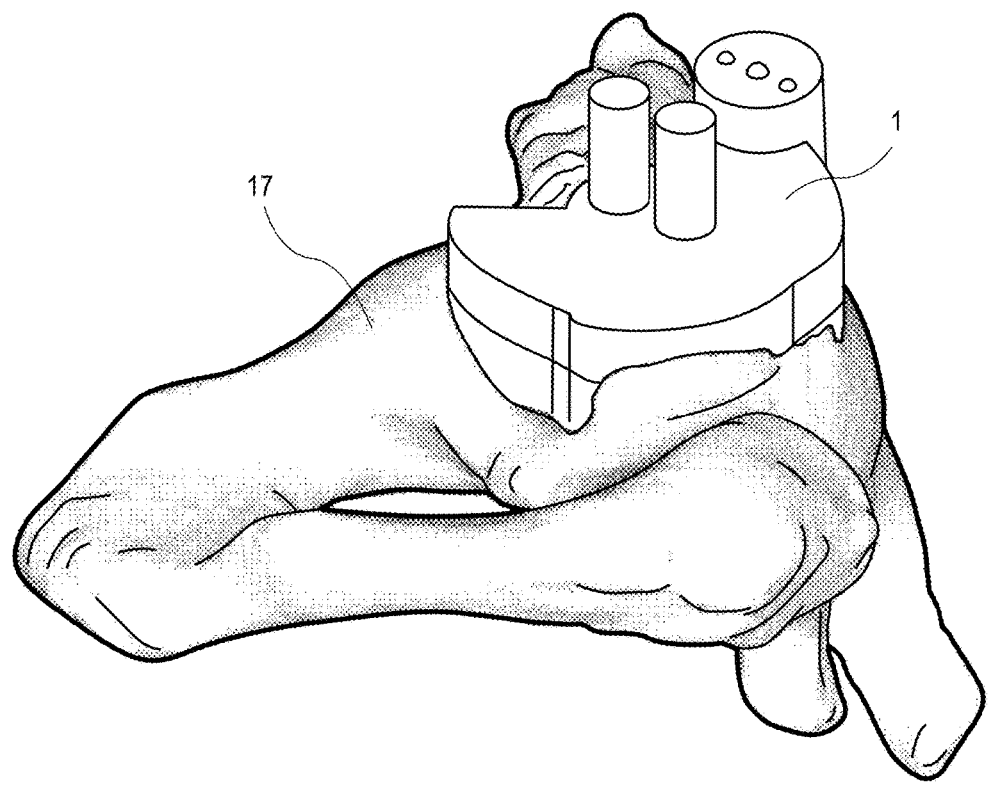

The surgical fixtures according to the present invention may comprise only one contact element. FIG. 4 A shows such a surgical fixture (1) according to a particular embodiment of the present invention. The fixture comprises a positioning element (3) and one contact element (2). The contact element comprises a patient-specific contact surface (4). The positioning element is attached to the contact element (2), and comprises a hole (5) for insertion of an alignment element and holes (6) for insertion of fixation elements. The hole (5) for insertion of an alignment element may also be used for drilling a hole in the pelvic bone. Thus, the positioning element is also a drill guide (9), more particularly a drilling cylinder. The connection between the positioning element (3) and the contact element (2) is adapted (not shown), such that the positioning element can be easily detached from the surgical fixture with surgical cutting instruments. The surgical fixture (1) further comprises two extensions (10), which are located on the contact element (2) and facilitate the rotational movement of the fixture during positioning. FIG. 4 B shows the same fixture (1), positioned on an acetabulum of a pelvic bone (17). The contact surface on the contact element of the fixture surrounds the acetabulum over an angle of more than 180°.

The invention claimed is:

1. A patient-specific surgical fixture for positioning an alignment element, comprising:
    one or more patient-specific contact elements configured to fit onto a socket of a ball-and-socket joint, the one or more patient-specific contact elements being configured to contact the socket, wherein a rim of the socket defines at least one of a substantially circular shape having a center defined by a circle best fitting the substantially circular shape or roughly elliptical shape having a center defined by an ellipse best fitting the roughly elliptical shape, wherein the one or more patient-specific contact elements, includes a first contact element, a second contact element, and a third contact element, each of the patient-specific contact elements is configured so that, when fit onto the socket, the first patient-specific contact element contacts the rim at a first contact point, the second patient-specific contact element contacts the rim at a second contact point, and the third patient-specific contact element contacts the rim at a third contact point, wherein a first angle defined by a first line connecting the first contact point and the center and a second line connecting the second contact point and the center measured in in a clockwise direction around the circle or ellipse best fitting the shape from the first line to the second line is not greater than 180°, wherein a second angle defined by the second line and a third line connecting the third contact point and the center measured in the clockwise direction from the second line to the third line is not greater than 180°, wherein a third angle defined by the third line and the first line measured in the clockwise direction from the third line to the first line is not greater than 180°, and wherein the sum of the first angle, the second angle, and the third angle is equal to 360°; and
    a positioning element having one or more holes, wherein at least one of the one or more holes is configured to receive the alignment element, and wherein the positioning element is detachably coupled to a connecting structure of the fixture,
    wherein one of the one or more patient-specific contact elements is configured to interact with an anatomical feature present on the socket when fit onto the socket, wherein the anatomical feature is one of a posterior notch of a transverse ligament or a coracoid process.

2. The surgical fixture according to claim 1, wherein the positioning element is one of the one or more patient-specific contact elements.

3. The surgical fixture according to claim 1, wherein the positioning element is configured to be broken from the connecting structure with surgical cutting instruments.

4. The surgical fixture according to claim 1, wherein the positioning element is detachably coupled to the connecting structure by at least one of a dovetail coupling, interlocking features, a pinned system, and a snap-fit mechanism.

5. The surgical fixture according to claim 1, wherein the positioning element and the one or more contact elements extended from the connecting structure.

6. The surgical fixture according to claim 1, wherein the positioning element comprises a drill guide.

7. The surgical fixture according to claim 1, wherein the one or more holes comprise at least two holes, and wherein a first and second hole of the one or more holes have a different diameter, wherein the first hole is the at least one of the one or more holes configured to receive the alignment element, and wherein the second hole is configured to receive a fixation element.

8. The surgical fixture according to claim 1, wherein the alignment element comprises at least one of a pin, a wire, a screw and a drill.

9. A method for a manufacture of patient-specific surgical fixtures according to claim 1, comprising the steps of:
   a) obtaining volume information of the socket of the ball-and-socket joint from a patient,
   b) obtaining the installation direction of a socket implant for the patient,
   c) identifying and selecting parts of a bone surrounding an implant zone which are suitable for inserting the alignment element,
   d) identifying and selecting parts of the bone in or surrounding the implant zone which are suitable for use as a base for a contact surface or surfaces of the surgical fixture, and
   e) designing and producing the surgical fixture based on the information obtained in steps a, b, c, and d.

10. A method for guiding a socket implant in a socket of a ball-and-socket joint, comprising the steps of:
   a) positioning a surgical fixture according to claim 1 onto the socket,
   b) using one of the holes provided by the fixture to insert a wire, pin, drill or screw into the bone surrounding the socket,
   c) removing the surgical fixture from the socket, and
   d) using the wire, pin, drill or screw to guide the implant in the correct direction onto the socket according to a pre-operational planning.

11. The method according to claim 10, wherein step a) involves a rotational movement of the fixture to obtain the desired orientation onto the socket and step c) comprises detaching the positioning element from the rest of the fixture and from the socket, so as to allow thereafter, a reversal of the rotational movement of step a) to remove the rest of the fixture from the socket.

12. The method according to claim 10, wherein the socket of the ball-and-socket joint is the acetabulum.

* * * * *